United States Patent [19]

Fuchs et al.

[11] 4,081,535
[45] Mar. 28, 1978

[54] O-ALKYL-O-[5-CHLORO-1,2,4-TRIAZOL(-3)yl]-THIONO(THIOL)-PHOSPHORIC (PHOSPHONIC) ACID ESTERS AND ESTER-AMIDES

[75] Inventors: Rainer Alois Fuchs, Wuppertal; Ingeborg Hammann, Cologne; Wolfgang Behrenz, Overath; Bernhard Homeyer, Leverkusen, all of Germany

[73] Assignee: Bayer Aktiengesellschaft, Leverkusen, Germany

[21] Appl. No.: 734,500

[22] Filed: Oct. 21, 1976

[30] Foreign Application Priority Data

Oct. 27, 1975 Germany .................. 2547971

[51] Int. Cl.² ............ A01N 9/36; A01N 13/00; C07F 9/65
[52] U.S. Cl. ................. 424/200; 260/308 R
[58] Field of Search .............. 260/308 R; 424/200

[56] References Cited

U.S. PATENT DOCUMENTS 3,809,701  5/1974  Dawes et al. ............ 260/308 R
3,867,396  2/1975  Dawes et al. ............ 260/308 R

FOREIGN PATENT DOCUMENTS 713,278  8/1954  United Kingdom ......... 260/308 R

Primary Examiner—Alton D. Rollins
Attorney, Agent, or Firm—Burgess, Dinklage & Sprung

[57] ABSTRACT

O-Alkyl-O-[5-chloro-1,2,4-triazol(3)yl]-thiono(thiol)-phosphoric (phosphonic) acid esters and ester-amides of the formula

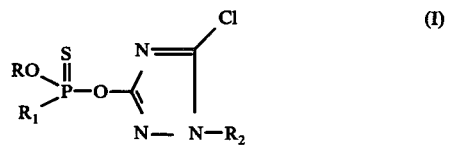

in which R is alkyl with 1 to 6 carbon atoms,
$R_1$ is alkyl, alkoxy, alkylthio or monoalkylamino each with 1 to 6 carbon atoms, and
$R_2$ is alkylthioalkyl with 1 to 4 carbon atoms per alkyl radical, alkenyl with 2 to 5 carbon atoms, carbalkoxyalkyl with 1 to 4 carbon atoms per alkyl radical, 1-methyl-2-cyanoethyl, or phenoxyalkyl with 1 to 4 carbon atoms in the alkyl radical and optionally substituted on the phenyl radical by at least one of halogen, cyano, or alkylthio or alkyl each with 1 to 4 carbon atoms, which possess arthropodicidal and nematicidal properties.

10 Claims, No Drawings

O-ALKYL-O-[5-CHLORO-1,2,4-TRIAZOL(3)yl]-THIONO(THIOL)-PHOSPHORIC (PHOSPHONIC) ACID ESTERS AND ESTER-AMIDES

The present invention relates to and has for its objects the provision of particular new O-alkyl-O-[5-chloro-1,2,4-triazol(3)yl]-thiono(thiol)-phosphoric (phosphonic) acid esters and ester-amides which possess arthropodicidal and nematicidal properties, active compositions in the form of mixtures of such compounds with solid and liquid dispersible carrier vehicles, and methods for producing such compounds and for using such compounds in a new way especially for combating pests, e.g. arthropods and nematodes, with other and further objects becoming apparent from a study of the within specification and accompanying examples.

It is known from German Published Specification DOS 2,301,400 that O-triazolylthionophosphoric-(phosphonic) acid esters, for example O,O-diethyl-O-[1-ethyl-5-cyanomethylthio- (Compound A) or 1-ethyl-5-allylthio-1,2,4-triazol(3)yl]-thionophosphoric acid ester (Compound B), O-ethyl-O-[1-methyl-5-methoxy-1,2,4-triazol(3)yl]-thionophenylphosphonic acid ester (Compound C) and O-ethyl-N-isopropyl-O-[1-isopropyl-5-methylthio-1,2,4-triazol(3)yl]-thionophosphoric acid esteramide (Compound D) possess insecticidal and acaricidal properties.

The present invention provides, as new compounds, the O-triazolylthiono(thiol)phosphoric(phosphonic) acid esters and ester-amides of the general formula

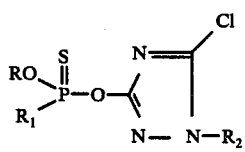

in which
R is alkyl with 1 to 6 carbon atoms,
R₁ is alkyl, alkoxy, alkylthio or monoalkylamino each with 1 to 6 carbon atoms, and
R₂ is alkylthioalkyl with 1 to 4 carbon atoms per alkyl radical, alkenyl with 2 to 5 carbon atoms, carbalkoxyalkyl with 1 to 4 carbon atoms per alkyl radical, 1-methyl-2-cyanoethyl, or phenoxyalkyl with 1 to 4 carbon atoms in the alkyl radical and optionally substituted on the phenyl radical by at least one of halogen, cyano, or alkylthio or alkyl each with 1 to 4 carbon atoms.

Preferably, R represents straight-chain or branched alkyl with 1 to 4 (especially 1 to 3) carbon atoms, R₁ represents straight-chain or branched alkyl, alkoxy, alkylthio or monoalkylamino each with 1 to 4 (especially 1 to 3) carbon atoms, and R₂ represents allyl, buten(2)yl, buten(3)yl, alkylthioethyl or alkylthiopropyl with 1 to 4 carbon atoms in the alkyl radical, 1-methyl-2-cyanoethyl, carbalkoxyalkyl with 1 to 3 carbon atoms per alkyl radical, phenoxyethyl, or halophenoxyethyl (especially chlorophenoxyethyl).

Surprisingly, the O-triazolylthiono(thiol)phosphoric-(phosphonic) acid esters and ester-amides according to the invention exhibit a better insecticidal, acaricidal and nematicidal action than the compounds of analogous structure and of the same type of action, previously known from the state of the art. They thus represent a genuine enrichment of the art.

Preferably, R represents straight-chain or branched alkyl with 1 to 4 (especially 1 to 3) carbon atoms, R₁ represents straight-chain or branched alkyl, alkoxy, alkylthio or monoalkylamino, each with 1 to 4 (especially 1 to 3) carbon atoms, and R₂ represents allyl, buten-(2)-yl, buten-(3)-yl, alkylthioethyl or alkylthiopropyl with 1 to 4 carbon atoms in the alkyl radical, 1-methyl-2-cyanoethyl, carbalkoxyalkyl with 1 to 3 carbon atoms per alkyl radical, or phenoxyethyl, the phenyl ring being optionally (but preferably) monosubstituted or polysubstituted by halogen (especially chlorine).

The present invention also provides a process for the preparation of an O-triazolylthiono(thiol)phosphoric-(phosphonic) acid ester or ester-amide of the formula (I), in which a thiono(thiol)phosphoric(phosphonic) acid ester halide or ester-amide halide of the general formula

in which
R and R₁ have the above-mentioned meanings and
Hal represents halogen, especially chlorine,
is reacted, if appropriate in the presence of a solvent or diluent, with a triazole derivative of the general formula

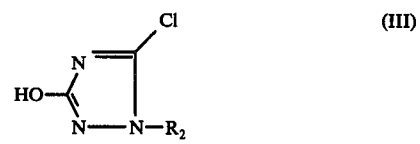

in which
R₂ has the above-mentioned meaning,
the latter being used as such, in the presence of an acid acceptor, or in the form of an alkali metal salt, alkaline earth metal salt or ammonium salt.

If, for example, O-ethyl-N-methylthionophosphoric acid ester-amide chloride and 1-(1-methyl-2-cyanoethyl)-3-hydroxy-5-chlorotriazole are used as starting materials, the course of the reaction can be represented by the following equation:

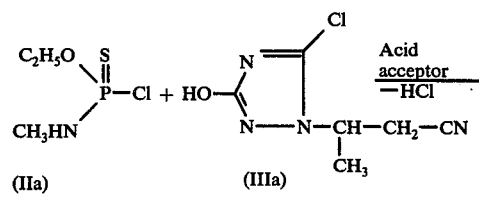

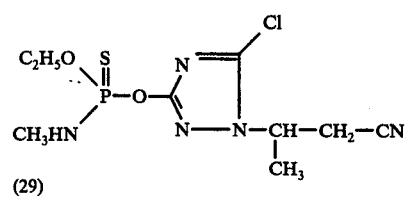

The thiono(thiol)phosphoric(phosphonic) acid ester halides and ester-amide halides (II) to be used as starting materials are known from the literature and can be prepared in accordance with generally customary processes.

The following may be mentioned as individual examples thereof: O,O-dimethyl-, O,O-diethyl-, O,O-di-n-propyl-, O,O-di-isopropyl-, O,O-di-n-butyl-, O,O-di-sec.-butyl-, O,O-di-isobutyl-, O,O-di-tert.-butyl-, O-methyl-O-ethyl-, O-ethyl-O-n-propyl-, O-ethyl-O-iso-propyl-, O-ethyl-O-tert.-butyl- or O-ethyl-O-sec.-butyl-thionophosphoric acid diester chloride; O,S-dimethyl-, O,S-diethyl-, O,S-di-n-propyl-, O,S-di-iso-propyl-, O,S-di-n-butyl-, O,S-di-isobutyl-, O,S-di-sec.-butyl-, O,S-di-tert.-butyl-, O-methyl-S-ethyl-, O-ethyl-S-n-propyl-, O-ethyl-S-isopropyl-, O-ethyl-S-n-butyl-, O-n-propyl-S-ethyl-, O-n-propyl-S-n-butyl- or O-isopropyl-S-ethyl-thionothiolphosphoric acid diester chloride; O-methyl-N-methyl-, O-ethyl-N-ethyl-, O-n-propyl-N-n-propyl-, O-iso-propyl-N-isopropyl-, O-n-butyl-N-n-butyl-, O-isobutyl-N-isobutyl-, O-sec.-butyl-N-sec.-butyl-, O-tert.-butyl-N-tert.-butyl-, O-ethyl-N-isopropyl-, O-iso-propyl-N-ethyl-, O-tert.-butyl-N-ethyl- or O-sec.-butyl-N-ethyl-thionophosphoric acid ester-amide chloride; and O-methyl-, O-ethyl-, O-n-propyl-, O-isopropyl-, O-n-butyl-, O-isobutyl-, O-sec.-butyl- or O-tert.-butyl-methane-, -ethane-, -n-propane-, -isopropane-, -n-butane-, -isobutane-, -sec.-butane- or -tert.-butane-thionophosphonic acid ester chloride.

The triazole derivatives of the formula (III) can be prepared in accordance with generally customary processes, in particular by reacting correspondingly substituted hydrazines or their hydrochlorides with N-chlorocarbonylisocyanide-dichloride in accordance with the following equation:

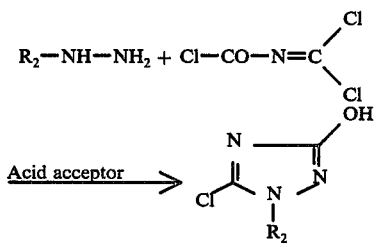

wherein
R$_2$ has the above-mentioned meaning.

The following may be mentioned as individual examples of triazole derivatives (III) to be reacted in accordance with the process: 1-(1-methyl-2-cyanoethyl)-, 1-allyl-, 1-[2-methylpropen(2)yl]-, 1-buten-(3)-yl-, 1-(2-methylthioethyl)-, 1-(2-ethylthioethyl)-, 1-(2-n-propyl-thioethyl)-, 1-(2-iso-propylthioethyl)-, 1-(2-n-butylthio-ethyl)-, 1-(2-sec.-butyl-thioethyl)-, 1-(2-iso-butylthioethyl)-, 1-(2-tert.-butylthio-ethyl)-, 1-(3-methylthio-n-propyl)-, 1-(3-ethylthio-n-propyl)-, 1-(3-n-propylthio-n-propyl)-, 1-(3-iso-propylthio-n-propyl)-, 1-(3-n-butylthio-n-propyl)-, 1-(3-tert.-butylthio-n-propyl)-, 1-(1-methylthioethyl)-, 1-(1-ethylthioethyl)-, 1-(iso-propylthiomethyl)-, 1-(ethylthiomethyl)-, 1-(2-phenoxyethyl)-, 1-[2-(2,4-dichlorophenoxy)-ethyl]-, 1-[2-(4-chlorophenoxy)-ethyl]-, 1-[2-(2,4,6-trichlorophenoxy)-ethyl]-, 1-[2-(3,4-dichlorophenoxy)-ethyl]-, 1- 8 2-(pentachlorophenoxy)-ethyl]-, 1-carbomethoxymethyl-, 1-carbethoxymethyl-, 1-carbo-n-propoxy-methyl-, 1-carbo-iso-propoxymethyl-, 1-(1-carbomethoxyethyl)-, 1-(1carbethoxyethyl)-, 1-(1-carbo-n-propoxyethyl)-, 1-(1-carbo-iso-propoxyethyl)-, 1-(1-carbomethoxy-n-propyl)-, 1-(1-carbethoxy-n-propyl)-, 1-(1-carbo-n-propoxy-n-propyl)- and 1-(1-carbo-iso-propoxy-n-propyl)-5-chloro-3-hydroxy-1,2,4-triazole.

The process for the preparation of the compounds according to the invention is preferably carried out in the presence of a suitable solvent or diluent. Practically all inert organic solvents can be used for this purpose, especially aliphatic and aromatic, optionally chlorinated, hydrocarbons such as benzene, toluene, xylene, benzine, methylene chloride, chloroform, carbon tetrachloride or chlorobenzene; ethers, for example diethyl ether, dibutyl ether and dioxane; ketones, for example acetone, methyl ethyl ketone, methyl isopropyl ketone and methyl isobutyl ketone; and nitriles, such as acetonitrile and propionitrile.

All customary acid-binding agents can be used as acid acceptors. Alkali metal carbonates and alkali metal alcoholates, such as sodium carbonate and potassium carbonate, sodium methylate and ethylate and potassium methylate and ethylate, have proved particularly suitable, as have aliphatic, aromatic or heterocyclic amines, for example triethylamine, trimethylamine, dimethylaniline, dimethylbenzylamine and pyridine.

The reaction temperature can be varied within a fairly wide range. In general, the reaction is carried out at between 0° and 120° C, preferably at from 30° to 75° C.

In general, the reaction is allowed to take place under normal pressure.

To carry out the process, the starting components are in general employed in equimolar amounts. An excess of one or other reactant produces no significant advantages. The reaction is preferably carried out in one of the above-mentioned solvents or diluents, in the presence of an acid acceptor, at the stated temperatures, while stirring. After a reaction time of from one to several hours, in most cases at an elevated temperature, the reaction mixture is worked up in accordance with generally customary methods.

The new compounds are obtained in the form of oils, which can frequently not be distilled without decomposition, but are freed from the last volatile constituents by so-called "slight distillation", that is to say by prolonged heating under reduced pressure to moderately elevated temperatures, and are purified in this way. They are characterized by the refractive index.

As already mentioned, the O-triazolylthiono(thiol)-phosphoric(phosphonic) acid esters and ester-amides according to the invention are distinguished by an excellent insecticidal, acaricidal and nematicidal activity. They are not only active against plant pests but also against pests harmful to health and pests of stored products. They have a low phytotoxicity and a good action against both sucking and biting insects and against mites.

For this reason, the compounds according to the invention can be employed successfully as pesticides in plant protection as well as in the hygiene field and the field of protection of stored products.

The active compounds are well tolerated by plants, have a favorable level of toxicity to warm-blooded animals, and can be used for combating arthropod pests, especially insects and arachnids, and nematode pests which are encountered in agriculture, in forestry, in the protection of stored products and of materials, and in the hygiene field. They are active against normally sensitive and resistant species and against all or some stages of development.

The above-mentioned pests include from the class of the *Isopoda*, for example, *Oniscus ascellus, Armadillidium vulgare* and *Porcellio scaber;* from the class of the *Diplopoda*, for example *Blaniulus guttulatus;* from the class of the *Chilopoda*, for example *Geophilus carpophagus* and *Scutigera* spec.; from the class of the *Symphyla*, for example *Scutigerella immaculata;* from the class of the *Thysanura*, for example *Lepisma saccharina;* from the class of the *Collembola*, for example *Onychiurus armatus;* from the class of the *Orthoptera*, for example *Blatta orientalis, Periplaneta americana, Leucophaea maderae, Blattella germanica, Acheta domesticus, Gryllotalpa* spp., *Locusta migratoria migratorioides, Melanoplus differentialis* and *Schistocerca gregaria;* from the class of the *Dermaptera*, for example *Forficula auricularia;* from the class of the *Isoptera*, for example *Reticulitermes* spp.; from the class of the *Anoplura*, for example *Phylloxera vastatrix, Pemphigus* spp., *Pediculus humanus corporis, Haematopinus* spp. and *Linognathus* spp.; from the class of the Mallophaga, for example *Trichodectes* spp. and *Damalinea* spp. from the class of the *Thysanoptera*, for example *Hercinothrips femoralis* and *Thrips tabaci;* from the class of the *Heteroptera*, for example *Eurygaster* spp., *Dysdercus intermedius, Piesma quadrata, Cimex lectularius, Rhodnius prolixus* and *Triatoma* spp.; from the class of the *Homoptera*, for example *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae, Myzus* spp., *Phorodon humuli, Rhopalosiphum padi, Empoasca* spp., *Euscelis bilobatus, Nephotettix cincticeps, Lecanium corni, Saissetia oleae, Laodelphax striatellus, Nilaparvata lugens, Aonidiella aurantii, Aspidiotus hederae, Pseudococcus* spp. and *Psylla* spp.; from the class of the *Lepidoptera*, for example *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea, Lymantria* spp., *Bucculatrix thurberiella, Phyllocnistis citrella, Agrotis* spp., *Euxoa* spp., *Feltia* spp., *Earias insulana, Heliothis* spp., *Laphygma exigua, Mamestra brassicae, Panolis flammea, Prodenia litura, Spodoptera* spp., *Trichoplusia ni, Carpocapsa pomonella, Pieris* spp., *Chilo* spp., *Pyrausta nubilalis, Ephestia kuebniella, Galleria mellonella, Cacoecia podana, Capua reticulana, Choristoneura fumiferana, Clysia ambiguella, Homona magnanima* and *Tortrix viridana;* from the class of the *Coleoptera*, for example *Anobium punctatum, Rhizopertha dominica, Bruchidius obtectus, Acanthoscelides obtectus, Hylotrupes bajulus, Agelastica alni, Leptinotarsa decemlineata, Phaedon cochleariae, Diabrotica* spp., *Psylliodes chrysocephala, Epilachna varivestis, Atomaria* spp., *Oryzaephilus surinamensis, Anthonomus* spp., *Sitophilus* spp., *Otiorrhynchus sulcatus, Cosmopolites sordidus, Ceuthorrhynchus assimilis, Hypera postica, Dermestes* spp., *Trogoderma* spp., *Anthrenus* spp., *Attagenus* spp., *Lyctus* spp., *Meligethes aeneus, Ptinus* spp., *Niptus hololeucus, Gibbium psylloides, Tribolium* spp., *Tenebrio molitor, Agriotes* spp., *Conoderus* spp., *Melolontha melolontha, Amphimallon solstitialis* and *Costelytra zealandica;* from the class of the *Hymenoptera*, for example *Diprion* spp., *Hoplocampa* spp., *Lasius* spp., *Monomorium pharanois* and *Vespa* spp.; from the class of the Diptera, for example *Aedes* spp., *Anopheles* spp., *Culex* spp., *Drosophila melanogaster Musca* spp., *Fannia* spp.; *Calliphora erythrocephala, Lucilia* spp., *Chrysomyia* spp., *Cuterebra* spp., *Gastrophilus* spp., *Hyppobosca* spp., *Stomoxys* spp., *Oestrus* spp., *Hypoderma* spp., *Tabanus* spp., *Tannia* spp., *Bibio hortulanus, Oscinella frit, Phorbia* spp., *Pegomyia hyoscyami, Ceratitis capitata, Dacus oleae* and *Tipula paludosa;* from the order of the Siphonaptera, for example *Xenopsylla cheopis* and *Ceratophyllus* spp.; from the class of the *Arachnida*, for example *Scorpio maurus* and *Latrodectus mactans;* from the class of the *Acarina*, for example *Acarus siro, Argas* spp., *Ornithodoros* spp., *Dermanyssus gallinae, Eriophyes ribis, Phyllocoptruta oleivora, Boophilus* spp., *Rhipicephalus* spp., *Amblyomma* spp., *Hyalomma* spp., *Ixodes* spp., *Psoroptes* spp., *Chorioptes* spp., *Sarcoptes* spp., *Tarsonemus* spp., *Bryobia praetiosa, Panonychus* spp. and *Tetranychus* spp.

The plant-parasitic nematodes include *Pratylenchus* spp., *Radopholus similis, Ditylenchus dipsaci, Tylenchulus semi-penetrans, Heterodera* spp., *Meloidogyne* spp., *Aphelenchoides* spp., *Longidorus* spp., *Xiphinema* spp., and *Trichodorus* spp.

When used against hygiene pests and pests of stored products, the active compounds are distinguished by an excellent residual activity on wood and clay as well as a good stability to alkali on limed substrates.

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, wettable powders, suspensions, powders, dusting agents, foams, pastes, soluble powders, granules, aerosols, suspension-emulsion concentrates, seed-treatment powders, natural and synthetic materials impregnated with active compound, very fine capsules in polymeric substances and in coating compositions, for use on seed, and formulations used with burning equipment, such as fumigating cartridges, fumigating cans, fumigating coils and the like, as well as ULV cold mist and warm mist formulations.

These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as halogenated hydrocarbons as well as butane, propane, nitrogen and carbon dioxide; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkanes, (e.g. cyclohexane, etc.), paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone, methyl isobutyl ketone, cyclohexanone, etc.), and/or water; as solid carriers, ground natural minerals, such as kaolins, clays, talc, chalk, quartz, attapulgite, montmorillonite or diatomaceous earth, and ground synthetic minerals, such as highly-dispersed silicic acid, alumina and silicates; as solid carriers for granules; crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents, such as lignin, sulfite waste liquors, methyl cellulose, etc.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

Such active compounds may be employed alone or in the form of mixtures with one another and/or with such solid and/or liquid dispersible carrier vehicles and/or with other known compatible active agents, especially plant protection agents, such as other arthropodicides and nematicides, or fungicides, bactericides, rodenticides, herbicides, fertilizers, growth-regulating agents, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application or field application generally contemplate those in which the active compound is present in an amount substantially between about 0.0000001–100, preferably 0.01–10%, by weight of the mixture. Thus, the present invention contemplates overall compositions which comprise mixtures of a conventional dispersible carrier such as (1) a dispersible inert finely divided carrier solid, and/or (2) a dispersible carrier liquid such as an inert organic solvent and/or water, preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001–95%, and preferably 0.01–95%, by weight of the mixture.

When used against nematodes, the preparations are generally applied to an area of agriculture in amounts of 1 to 100 kg of active compound per hectare, and are then incorporated into the soil.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50–100 microns, or even less, i.e mist form, for example by airplane crop spraying techniques. Only up to at most about a few liters/hectare are needed, and often amounts only up to about 15 to 100 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20–100% by weight of the active compound.

Furthermore, the present invention contemplates methods of selectively killing, combating or controlling pests, e.g. arthropods such as insects and acarids, or nematodes, which comprises applying to at least one of correspondingly (a) such arthropods, (b) such nematodes, and (c) the corresponding habitat thereof, i.e. the locus to be protected, e.g. to a growing crop, to an area where a crop is to be grown or to a domestic animal, a correspondingly combative or toxic amount, i.e. an arthropodicidally or nematicidally effective amount, of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, and the like.

It will be realized, of course, that the concentration of the particular active compound utilized in admixture with the carrier vehicle will depend upon the intended application. Therefore, in special cases it is possible to go above or below the aforementioned concentration ranges.

The unexpected superiority and outstanding activity of the particular new compounds of the present invention are illustrated, without limitation, by the following examples:

EXAMPLE 1

Drosophila test

Solvent: 3 parts by weight of acetone
Emulsifier: 1 part by weight of alkylaryl polyglycol ether To produce a suitable preparation of active compound, 1 part by weight of the active compound was mixed with the stated amount of solvent containing the stated amount of emulsifier, and the concentrate was diluted with water to the desired concentration.

1 cm$^3$ of the preparation of the active compound was applied with a pipette to a filter paper disc of 7 cm diameter. The wet disc was placed over the orifice of a glass vessel containing 50 vinegar flies (*Drosophila melanogaster*) and covered with a glass plate.

After the specified periods of time, the destruction was determined in %. 100% means that all the flies were killed; 0% means that no flies were killed.

The active compounds, the concentrations of the active compounds, the evaluation times and the results can be seen from the following table:

Table 1

(Drosophila test)

| Active compound | Active compound concentration in % | Degree of destruction in % after 1 day |
|---|---|---|
| 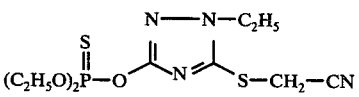 (known) (A) | 0.1<br>0.01<br>0.001 | 10C<br>10C<br>0 |
| 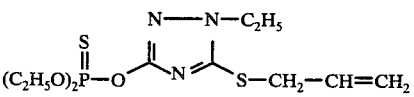 (known) (B) | 0.1<br>0.01<br>0.001 | 100<br>100<br>0 |
| 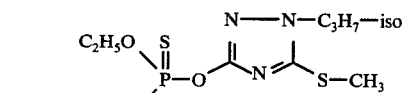 (known) (D) | 0.1<br>0.01<br>0.001 | 100<br>40<br>0 |
| 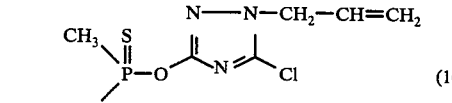 (16) | 0.1<br>0.01<br>0.001 | 100<br>100<br>90 |
| 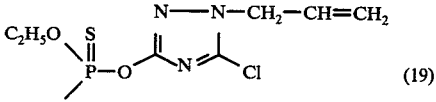 (19) | 0.1<br>0.01<br>0.001 | 100<br>100<br>95 |
| 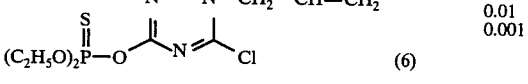 (6) | 0.1<br>0.01<br>0.001 | 100<br>100<br>100 |
| 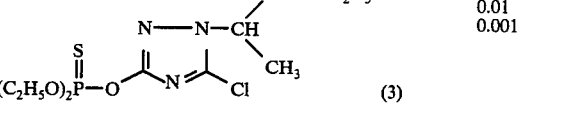 (3) | 0.1<br>0.01<br>0.001 | 100<br>100<br>100 |
| 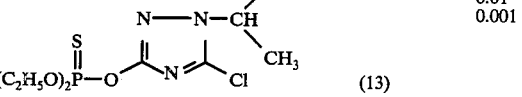 (13) | 0.1<br>0.01<br>0.001 | 100<br>100<br>100 |

EXAMPLE 2

Phaedon larvae test

Solvent: 3 parts by weight of acetone

Emulsifier: 1 part by weight of alkylaryl polyglycol ether

To produce a suitable preparation of active compound, 1 part by weight of the active compound was mixed with the stated amount of solvent containing the stated amount of emulsifier and the concentrate was diluted with water to the desired concentration.

Cabbage leaves (*Brassica oleracea*) were sprayed with the preparation of the active compound until dripping wet and were then infested with mustard beetle larvae (*Phaedon cochleariae*).

After the specified periods of time, the degree of destruction was determined in %: 100% means that all the beetle larvae had been killed whereas 0% means that none of the beetle larvae had been killed.

The active compounds, the concentrations of the active compounds, the evaluation times and the results can be seen from the following table:

Table 2

(*Phaedon* larvae test)

| Active compound | Active compound concentration in % | Degree of destruction in % after 3 days |
|---|---|---|
| Phenyl(ethoxy)phosphinothioyl derivative with N=C(N-CH₃)-N=C(OCH₃)- (known) (C) | 0.1<br>0.01 | 100<br>0 |
| Methyl(iso-C₃H₇O)phosphinothioyl-O-C(=N-N=C(Cl)-CH₂-CH₂-SC₂H₅) (8) | 0.1<br>0.01 | 100<br>100 |
| (C₂H₅O)₂P(S)-O-C(=N-N=C(Cl)-CH₂-CH₂-SC₂H₅) (1) | 0.1<br>0.01 | 100<br>100 |
| C₂H₅O(n-C₃H₇O)P(S)-O-C(=N-N=C(Cl)-CH₂-CH₂-SC₂H₅) (9) | 0.1<br>0.01 | 100<br>100 |
| C₂H₅O(n-C₃H₇S)P(S)-O-C(=N-N=C(Cl)-CH₂-CH₂-SC₂H₅) (7) | 0.1<br>0.01 | 100<br>90 |
| CH₃(iso-C₃H₇O)P(S)-O-C(=N-N=C(Cl)-CH₂-CH₂-SC₃H₇-iso) (17) | 0.1<br>0.01 | 100<br>100 |
| C₂H₅(C₂H₅O)P(S)-O-C(=N-N=C(Cl)-CH₂-CH₂-SC₃H₇-iso) (12) | 0.1<br>0.01 | 100<br>100 |
| (C₂H₅O)₂P(S)-O-C(=N-N=C(Cl)-CH₂-CH₂-SC₃H₇-iso) (11) | 0.1<br>0.01 | 100<br>100 |
| CH₃(iso-C₃H₇O)P(S)-O-C(=N-N=C(Cl)-CH₂-CH₂-O-C₆H₅) (2) | 0.1<br>0.01 | 100<br>100 |
| (C₂H₅O)₂P(S)-O-C(=N-N=C(Cl)-CH₂-CH₂-O-C₆H₅) (4) | 0.1<br>0.01 | 100<br>100 |

Table 2-continued (*Phaedon* larvae test)

| Active compound | Active compound concentration in % | Degree of destruction in % after 3 days |
|---|---|---|
| (5) structure with $C_2H_5O$, $n-C_3H_7O$, P=S, N—N—CH$_2$—CH$_2$—O—phenyl, Cl | 0.1 / 0.01 | 100 / 100 |
| (3) structure with $(C_2H_5O)_2P(=S)$—O—, N—N—CH(CO—OC$_2$H$_5$)(CH$_3$), Cl | 0.1 / 0.01 | 100 / 100 |
| (13) structure with $(C_2H_5O)_2P(=S)$—O—, N—N—CH(CH$_2$—CN)(CH$_3$), Cl | 0.1 / 0.01 | 100 / 100 |
| (6) structure with $(C_2H_5O)_2P(=S)$—O—, N—N—CH$_2$—CH=CH$_2$, Cl | 0.1 / 0.01 | 100 / 100 |
| (26) structure with CH$_3$, i-C$_3$H$_7$O, P=S, N—N—CH$_2$—CH$_2$O—(4-Cl-phenyl), Cl | 0.1 / 0.01 | 100 / 100 |
| (23) structure with $C_2H_5$, $C_2H_5O$, P=S, N—N—CH$_2$—CH$_2$O—(2,4-diCl-phenyl), Cl | 0.1 / 0.01 | 100 / 100 |
| (21) structure with $(C_2H_5O)_2P(=S)$—O—, N—N—CH$_2$—CH$_2$O—(2,4-diCl-phenyl), Cl | 0.1 / 0.01 | 100 / 100 |

EXAMPLE 3

Myzus test (contact action)

Solvent: 3 parts by weight of acetone
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Cabbage plants (*Brassica oleracea*) which had been heavily infested with peach aphids (*Myzus persicae*) were sprayed with the preparation of the active compound until dripping wet.

After the specified periods of time, the degree of destruction was determined as a percentage: 100% means that all the aphids were killed whereas 0% means that none of the aphids were killed.

The active compounds, the concentrations of the active compounds, the evaluation times and the results can be seen from the following table:

Table 3

(*Myzus* test)

| Active compound | Active compound concentration in % | Degree of destruction in % after 1 day |
|---|---|---|
| [structure with C₂H₅O, S, P, phenyl, O, N=N-CH₃, N, OCH₃] (known) (C) | 0.1<br>0.01 | 100<br>0 |
| [structure (C₂H₅O)₂P(S)-O-C(=N-N-CH₂-CH₂-SC₂H₅)-N=CCl] (1) | 0.1<br>0.01 | 100<br>100 |
| [structure C₂H₅O, n-C₃H₇O, P(S)-O-C(=N-N-CH₂-CH₂-SC₂H₅)-N=CCl] (9) | 0.1<br>0.01 | 100<br>100 |
| [structure C₂H₅, C₂H₅O, P(S)-O-C(=N-N-CH₂-CH₂-SC₃H₇-iso)-N=CCl] (12) | 0.1<br>0.01 | 100<br>100 |
| [structure (C₂H₅O)₂P(S)-O-C(=N-N-CH₂-CH₂-SC₃H₇-iso)-N=CCl] (11) | 0.1<br>0.01 | 100<br>100 |
| [structure CH₃, iso-C₃H₇O, P(S)-O-C(=N-N-CH₂-CH₂-O-phenyl)-N=CCl] (2) | 0.1<br>0.01 | 100<br>100 |
| [structure (C₂H₅O)₂P(S)-O-C(=N-N-CH₂-CH₂-O-phenyl)-N=CCl] (4) | 0.1<br>0.01 | 100<br>99 |
| [structure C₂H₅O, n-C₃H₇O, P(S)-O-C(=N-N-CH₂-CH₂-O-phenyl)-N=CCl] (5) | 0.1<br>0.01 | 100<br>100 |
| [structure (C₂H₅O)₂P(S)-O-C(=N-N-CH(CH₃)-CO-OC₂H₅)-N=CCl] (3) | 0.1<br>0.01 | 100<br>100 |
| [structure (C₂H₅O)₂P(S)-O-C(=N-N-CH(CH₃)-CH₂-CN)-N=CCl] (13) | 0.1<br>0.01 | 100<br>100 |

Table 3-continued

| Active compound | (*Myzus* test) Active compound concentration in % | Degree of destruction in % after 1 day |
|---|---|---|
| 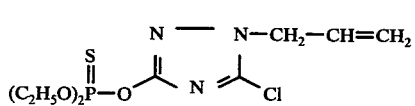 (6) | 0.1<br>0.01 | 100<br>100 |
| 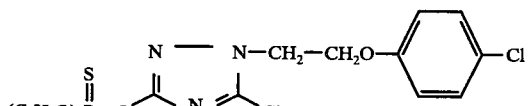 (25) | 0.1<br>0.01 | 100<br>100 |
| 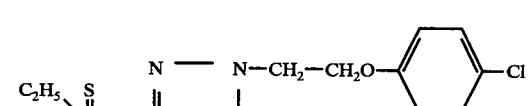 (24) | 0.1<br>0.01 | 100<br>100 |
| 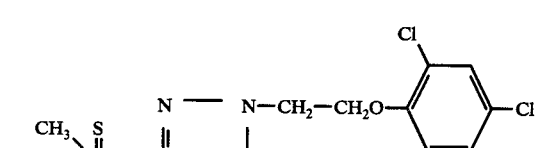 (22) | 0.1<br>0.01 | 100<br>100 |
| 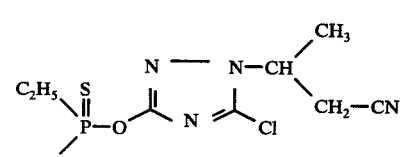 (15) | 0.1<br>0.01 | 100<br>100 |
| 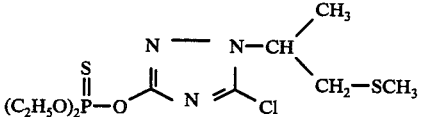 (27) | 0.1<br>0.01 | 100<br>100 |

EXAMPLE 4

Tetranychus test (resistant)

Solvent: 3 parts by weight Aceton
Emulsifier: 1 part by weight of alkylaryl polyglycol ether To produce a suitable preparation of active compound, 1 part by weight of the active compound was mixed with the stated amount of solvent and the stated amount of emulsifier and the concentrate was diluted with water to the desired concentration.

Bean plants (*Phaseolus vulgaris*) which were heavily infested with the two-spotted spider mite (*Tetranychus urticae*) in all stages of development were sprayed with the preparation of the active compound until dripping wet.

After the specified periods of time, the degree of destruction was determined as a percentage: 100% means that all the spider mites were killed whereas 0% means that none of the spider mites were killed.

The active compounds, the concentrations of the active compounds, the evaluation times and the results can be seen from the following table:

Table 4

(*Tetranychus* test)

| Active compound | Active compound concentration in % | Degree of destruction in % after 2 days |
|---|---|---|
| [Structure: phenyl-P(=S)(OC₂H₅)-O-C(=N-N=C(OCH₃)-N-CH₃)] (known) | 0.1<br>0.01 | 95<br>0 |
| [Structure: (C₂H₅O)₂P(=S)-O-C(=N-N=C(Cl)-N-CH(CH₃)(CH₂CN)] (13) | 0.1<br>0.01 | 100<br>99 |
| [Structure: CH₃(iso-C₃H₇O)P(=S)-O-C(=N-N=C(Cl)-N-CH₂-CH₂-SC₂H₅)] (8) | 0.1<br>0.01 | 100<br>80 |
| [Structure: CH₃(iso-C₃H₇O)P(=S)-O-C(=N-N=C(Cl)-N-CH₂-CH₂-SC₃H₇-iso)] (17) | 0.1<br>0.01 | 100<br>99 |
| [Structure: CH₃(iso-C₃H₇O)P(=S)-O-C(=N-N=C(Cl)-N-CH₂-CH₂-O-phenyl)] (2) | 0.1<br>0.01 | 99<br>98 |
| [Structure: C₂H₅(C₂H₅O)P(=S)-O-C(=N-N=C(Cl)-N-CH(CH₃)(CH₂-CN))] (15) | 0.1<br>0.01 | 100<br>100 |
| [Structure: (C₂H₅O)₂P(=S)-O-C(=N-N=C(Cl)-N-CH(CH₃)(CH₂-SCH₃))] (27) | 0.1<br>0.01 | 100<br>100 |

EXAMPLE 5

Test insect: *Tenebrio molitor* larvae in the soil
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with the soil. The concentration of the active compound in the preparation was practically immaterial, the only decisive factor being the amount by weight of active compound per unit volume of soil, which is quoted hereinafter in ppm (= mg/1). The soil was filled into pots and the pots were left to stand at room temperature.

After 24 hours the test insects were introduced into the treated soil and after a further 2 to 7 days the degree of effectiveness of the active compound was determined in % by counting the dead and live test insects. The degree of effectiveness is 100% if all test insects had been killed and is 0% if exactly as many test insects were still alive as in the case of the untreated control.

The active compounds, amounts used and results can be seen from the table which follows:

Table 5

*(Tenebrio molitor larvae in the soil)*

| Active compound | Degree of destruction in % at an active compound concentration of 10 ppm |
|---|---|
| $C_2H_5O\diagdown \overset{S}{\underset{\|}{P}}-O-\overset{N=\!=\!=N-C_3H_7\text{-iso}}{\underset{\diagdown N \diagup}{\bigg\langle}}\!\!-S-CH_3$ <br> iso-$C_3H_7$—NH ⁄ <br> (known) (D) | 0 |
| $(C_2H_5O)_2\overset{S}{\underset{\|}{P}}-O-\overset{N=\!=\!=N-CH_2-CH_2-SC_3H_7\text{-iso}}{\underset{\diagdown N \diagup}{\bigg\langle}}\!\!-Cl$ <br> (11) | 100 |
| $(C_2H_5O)_2\overset{S}{\underset{\|}{P}}-O-\overset{N=\!=\!=N-CH(CH_2-CN)(CH_3)}{\underset{\diagdown N \diagup}{\bigg\langle}}\!\!-Cl$ <br> (13) | 100 |

EXAMPLE 6

Test insect: Phorbia antiqua grubs in the soil
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with the soil. The concentration of the active compound in the preparation was practically immaterial, the only decisive factor being the amount by weight of active compound per unit volume of soil, which is quoted hereinafter in ppm (= mg/1). The soil was filled into pots and the pots were left to stand at room temperature.

After 24 hours the test insects were introduced into the treated soil and after a further 2 to 7 days the degree of effectiveness of the active compound was determined in % by counting the dead and live test insects. The degree of effectiveness is 100% if all test insects had been killed and is 0% if exactly as many test insects were still alive as in the case of the untreated control.

The active compounds, amounts used and results can be seen from the table which follows:

Table 6

*(Phorbia antiqua grubs in the soil)*

| Active compound | Degree of destruction in % at an active compound concentration of 10 ppm |
|---|---|
| Phenyl-$\overset{S}{\underset{\|}{P}}(OC_2H_5)-O-\overset{N=\!=\!=N-CH_3}{\underset{\diagdown N \diagup}{\bigg\langle}}\!\!-OCH_3$ <br> (known) (C) | 0 |
| $C_2H_5O\diagdown \overset{S}{\underset{\|}{P}}-O-\overset{N=\!=\!=N-C_3H_7\text{-iso}}{\underset{\diagdown N \diagup}{\bigg\langle}}\!\!-S-CH_3$ <br> iso-$C_3H_7$—NH ⁄ <br> (known) (D) | 0 |
| $(C_2H_5O)_2\overset{S}{\underset{\|}{P}}-O-\overset{N=\!=\!=N-CH_2-CH_2-O\text{-phenyl}}{\underset{\diagdown N \diagup}{\bigg\langle}}\!\!-Cl$ <br> (4) | 100 |

Table 6-continued
(*Phorbia antiqua* grubs in the soil)

| Active compound | Degree of destruction in % at an active compound concentration of 10 ppm |
|---|---|
| (C₂H₅O)₂P(S)—O—C(=N—N(CH₂CH₂SC₂H₅)—N=CCl) (1) | 100 |
| C₂H₅O(n-C₃H₇S)P(S)—O—C(=N—N(CH₂CH₂SC₂H₅)—N=CCl) (7) | 100 |
| CH₃(iso-C₃H₇O)P(S)—O—C(=N—N(CH₂CH₂SC₂H₅)—N=CCl) (8) | 100 |
| CH₃(iso-C₃H₇O)P(S)—O—C(=N—N(CH₂CH₂—O—C₆H₅)—N=CCl) (2) | 100 |
| C₂H₅O(n-C₃H₇O)P(S)—O—C(=N—N(CH₂CH₂—O—C₆H₅)—N=CCl) (5) | 100 |
| (C₂H₅O)₂P(S)—O—C(=N—N(CH₂CH₂SC₃H₇-iso)—N=CCl) (11) | 100 |
| (C₂H₅O)₂P(S)—O—C(=N—N(CH(CH₃)CH₂CN)—N=CCl) (13) | 100 |
| CH₃(iso-C₃H₇O)P(S)—O—C(=N—N(CH₂CH₂—SC₃H₇-iso)—N=CCl) (17) | 100 |
| CH₃(iso-C₃H₇O)P(S)—O—C(=N—N(CH₂—CH=CH₂)—N=CCl) (16) | 100 |
| C₂H₅O(C₂H₅)P(S)—O—C(=N—N(CH₂—CH=CH₂)—N=CCl) (19) | 100 |

EXAMPLE 7

Test nematode: *Meloidogyne incognita*
Solvent: 3 parts by weight of acetone
Emulsifier: 1 part by weight of alkyl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with soil which was heavily infested with the test nematodes. The concentration of the active compound in the preparation was of practically no importance; only the amount of active compound per unit volume of soil, which is given hereinafter in ppm (= mg/l), was decisive. The treated soil was filled into pots, lettuce was sown in and the pots were kept at a greenhouse temperature of 27° C.

After 4 weeks, the lettuce roots were examined for infestation with nematodes (root galls), and the degree of effectiveness of the active compound was determined as a percentage. The degree of effectiveness was 100% when infestation had been completely avoided; it was 0% when the infestation was exactly the same as in the case of the control plants in untreated soil which had been infested in the same manner.

The active compounds, the amounts applied and the results can be seen from the following table:

Table 7

| Active compound | Degree of destruction in % at an active compound concentration of 5 ppm |
|---|---|
| 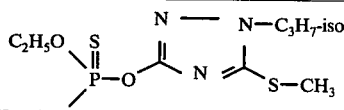 (known) (D) | 0 |
| 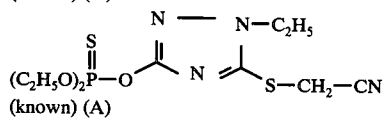 (known) (A) | 0 |
| 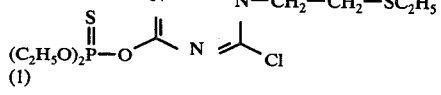 (I) | 100 |
| 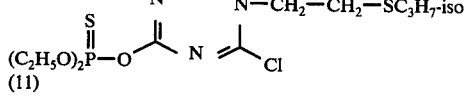 (II) | 100 |

EXAMPLE 8

$LT_{100}$ test for *Diptera*
Test insects: *Musca domestica*
Solvent: Acetone 2 parts by weight of active compound were taken up in 1000 parts by volume of solvent. The solution so obtained was diluted with further solvent to the desired lower concentrations.

2.5 ml of the solution of active compound were pipetted into a Petri dish. On the bottom of the Petri dish there was a filter paper with a diameter of about 9.5 cm. The Petri dish remained uncovered until the solvent had completely evaporated. The amount of active compound per square meter of filter paper varied with the concentration of the solution of active compound used. About 25 test insects were then placed in the Petri dish and it was covered with a glass lid.

The condition of the test insects was continuously observed. The time which was necessary for a 100% knock down effect was determined.

The test insects, the active compounds, the concentrations of the active compounds and the periods of time at which there was a 100% knock down effect can be seen from the following table:

Table 8

($LT_{100}$ test for *Diptera/Musca domestica*)

| Active compound | Active compound concentration of the solution in % | $LT_{100}$ in minutes (') or hours (hrs) |
|---|---|---|
| 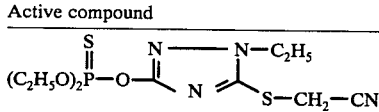 (known) (A) | 0.2 | 235' |
| 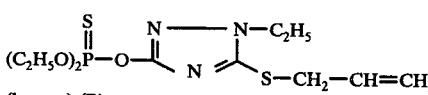 (known) (B) | 0.2 | 210' |

Table 8-continued
(LT$_{100}$ test for *Diptera/Musca domestica*)

| Active compound | Active compound concentration of the solution in % | LT$_{100}$ in minutes (') or hours (hrs) |
|---|---|---|
| (D) (known): $C_2H_5O$–P(=S)(–NH–iso-$C_3H_7$)–O–C(=N–)–N(–$C_3H_7$-iso)–C(=N)–S–$CH_3$ | 0.2 | 4 hrs = 80% |
| (6): $(C_2H_5O)_2$P(=S)–O–C(=N–)–N(–$CH_2$–CH=$CH_2$)–C(=N)–Cl | 0.02 | 120' |
| (11): $(C_2H_5O)_2$P(=S)–O–C(=N–)–N(–$CH_2$–$CH_2$–$SC_3H_7$-iso)–C(=N)–Cl | 0.2 | 150' |
| (12): $C_2H_5$/$C_2H_5O$–P(=S)–O–C(=N–)–N(–$CH_2$–$CH_2$–$SC_3H_7$-iso)–C(=N)–Cl | 0.2 | 90' |
| (13): $(C_2H_5O)_2$P(=S)–O–C(=N–)–N(–CH($CH_2$–CN)($CH_3$))–C(=N)–Cl | 0.02 | 100' |
| (8): $CH_3$/iso-$C_3H_7O$–P(=S)–O–C(=N–)–N(–$CH_2$–$CH_2$–$SC_2H_5$)–C(=N)–Cl | 0.2 | 140' |
| (2): $CH_3$/iso-$C_3H_7O$–P(=S)–O–C(=N–)–N(–$CH_2$–$CH_2$–O–$C_6H_5$)–C(=N)–Cl | 0.2 | 110' |
| (19): $C_2H_5O$/$C_2H_5$–P(=S)–O–C(=N–)–N(–$CH_2$–CH=$CH_2$)–C(=N)–Cl | 0.2 / 0.02 | 75' / 140' |
| (16): $CH_3$/iso-$C_3H_7O$–P(=S)–O–C(=N–)–N(–$CH_2$–CH=$CH_2$)–C(=N)–Cl | 0.2 | 85' |

EXAMPLE 9

Test insects: *Sitophilus granarius*
Solvent: Acetone 2 parts by weight of the active compound were taken up in 1,000 parts by volume of the solvent. The solution so obtained was diluted with further solvent to the desired concentrations.

2.5 ml of the solution of the active compound were pipetted into a Petri dish. On the bottom of the Petri dish there was a filter paper with a diameter of about 9.5 cm. The Petri dish remained uncovered until the solvent had completely evaporated. The amount of active compound per m² of filter paper varied with the concentration of the solution of active compound. About 25 test insects were then placed in the Petri dish and it was covered with a glass lid.

The condition of the test insects was observed 3 days after the commencement of the experiments. The destruction, in %, was determined. 100% denotes that all test insects has been killed; 0% denotes that no test insects had been killed.

The active compounds, the concentrations of the active compounds, the test insects and the results can be seen from the following table:

TABLE 9
*(Sitophilus granarius)*

| Active compound | Active compound concentration of the solution in % | Degree of destruction in % |
|---|---|---|
| (known) (C) — phenyl-P(S)(OC$_2$H$_5$)-O-C(=N-N(CH$_3$)-C(OCH$_3$)=N-) | 0.2 | 90% |
| (13) (C$_2$H$_5$O)$_2$P(S)-O-C(=N-N(CH(CH$_2$CN)CH$_3$)-C(Cl)=N-) | 0.02 | 100 |
| (12) C$_2$H$_5$(C$_2$H$_5$O)P(S)-O-C(=N-N(CH$_2$CH$_2$SC$_3$H$_7$-iso)-C(Cl)=N-) | 0.02 | 90 |
| (9) C$_2$H$_5$O(n-C$_3$H$_7$O)P(S)-O-C(=N-N(CH$_2$CH$_2$SC$_2$H$_5$)-C(Cl)=N-) | 0.02 | 100 |
| (2) CH$_3$(iso-C$_3$H$_7$O)P(S)-O-C(=N-N(CH$_2$CH$_2$-O-C$_6$H$_5$)-C(Cl)=N-) | 0.02 | 100 |
| (8) CH$_3$(iso-C$_3$H$_7$O)P(S)-O-C(=N-N(CH$_2$CH$_2$SC$_2$H$_5$)-C(Cl)=N-) | 0.02 | 100 |
| (6) (C$_2$H$_5$O)$_2$P(S)-O-C(=N-N(CH$_2$-CH=CH$_2$)-C(Cl)=N-) | 0.02 | 100 |
| (5) C$_2$H$_5$O(n-C$_3$H$_7$O)P(S)-O-C(=N-N(CH$_2$CH$_2$-O-C$_6$H$_5$)-C(Cl)=N-) | 0.02 | 100 |
| (1) (C$_2$H$_5$O)$_2$P(S)-O-C(=N-N(CH$_2$CH$_2$SC$_2$H$_5$)-C(Cl)=N-) | 0.02 | 100 |
| (4) (C$_2$H$_5$O)$_2$P(S)-O-C(=N-N(CH$_2$CH$_2$-O-C$_6$H$_5$)-C(Cl)=N-) | 0.02 | 80 |
| (19) C$_2$H$_5$O(C$_2$H$_5$)P(S)-O-C(=N-N(CH$_2$-CH=CH$_2$)-C(Cl)=N-) | 0.02 | 100 |

TABLE 9-continued
(Sitophilus granarius)

| Active compound | Active compound concentration of the solution in % | Degree of destruction in % |
|---|---|---|
| 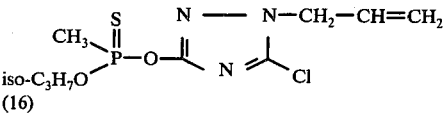 (16) | 0.02 | 100 |
| 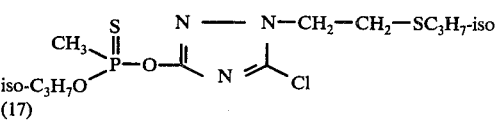 (17) | 0.02 | 100 |

The process of the present invention is illustrated by the following preparative examples:

EXAMPLE 10

The starting materials of the formula (III) were prepared, for example, as follows:

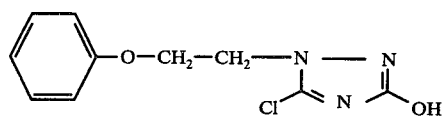 (a)

30.4 g (0.2 mole) of 2-phenoxyethylhydrazine were dissolved in 200 ml of anhydrous acetonitrile and 7.3 g of hydrogen chloride gas were passed in at 0° C. 32 g (0.2 mole) of N-chlorocarbonyl-isocyanide-dichloride were then added dropwise to the mixture at 15°–20° C, while cooling and stirring vigorously, and after completion of the addition, 30 g of potassium carbonate were also added. The batch was next stirred for 4 hours at room temperature, in the course of which the temperature in the reaction vessel at times rose to as much as 45° C, and was then heated under reflux until no further evolution of hydrogen chloride was detectable (4–6 hours). After cooling, the residue was filtered off and washed with acetonitrile, and the total filtrate was evaporated under reduced pressure. The crystalline residue was recrystallized from a little ethanol. 21 g (43.8% of theory) of 1-(2-phenoxyethyl)-5-chloro-3-hydroxy-1,2,4-triazole of melting point 166° C were obtained.

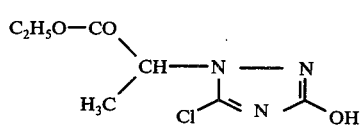 (b)

33.7 g (0.2 mole) of 1-hydrazinopropionic acid ethyl ester hydrochloride were dissolved in 150 ml of anhydrous acetonitrile and 32 g (0.2 mole) of N-chlorocarbonyl-isocyanide-dichloride were added dropwise to the mixture at 20° C. After completion of the addition, 30 g of potassium carbonate were added to the reaction mixture, and the latter was stirred for 3 hours at room temperature. The batch was then heated under reflux until no further evolution of hydrogen chloride was detectable (4–6 hours). After cooling, the residue was filtered off and washed with acetonitrile and the entire filtrate was evaporated under reduced pressure.

The crystalline residue was recrystallized from a little ethanol. 16.3 g (37% of theory) of 1-(1-carbethoxyethyl)-5-chloro-3-hydroxy-1,2,4-thiazole of melting point 141°–142° C were obtained.

The following compounds were prepared analogously to the procedure described in (a) and (b):

| Formula | Yield (% of theory) | Physical data (refractive index; melting point) |
|---|---|---|
| CH$_2$=CH—CH$_2$—N—N (triazole ring with Cl, OH) | 26 | 125 – 130° C |
| C$_2$H$_5$S—CH$_2$—CH$_2$—N—N (triazole ring with Cl, OH) | 41 | $n_D^{26}$: 1.5445 |
| iso-C$_3$H$_7$S—CH$_2$—CH$_2$—N—N (triazole ring with Cl, OH) | 69.9 | 75 – 77° C |
| NC—CH$_2$—CH(CH$_3$)—N—N (triazole ring with Cl, OH) | 43.5 | partially crystalline |
| C$_2$H$_5$O—CO—CH$_2$—N—N (triazole ring with Cl, OH) | 48.7 | 133 – 137° C |
| Cl—C$_6$H$_4$—O—CH$_2$—CH$_2$—N—N (triazole ring with Cl, OH) | 71.2 | 155° C |

-continued

| Formula | Yield (% of theory) | Physical data (refractive index; melting point) |
|---|---|---|
| 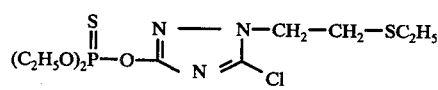 | 80.1 | 181° C |
| CH₃—S—CH₂—CH(CH₃)—N—N=C(Cl)—N=C(OH) (triazole) | 62.3 | 146° C |

EXAMPLE 11

$$(C_2H_5O)_2\overset{S}{\underset{\|}{P}}-O-\overset{N-N-CH_2-CH_2-SC_2H_5}{\underset{N}{\diagdown}}\overset{}{\diagup}Cl \quad (1)$$

13 g of O,O-diethylthionophosphoric acid diester chloride were added dropwise, while stirring, to a mixture of 14.5 g (0.07 mole) of 1-(2-ethylmercaptoethyl)-5-chloro-3-hydroxy-1,2,4-triazole, 7 g of triethylamine and 100 ml of absolute acetonitrile. The reaction mixture was warmed to 60° C for 2 hours and was then cooled and the batch was added to 200 ml of water and extracted with 200 ml of toluene. The organic phase was separated off and dried over sodium sulfate and the solvent was stripped off under reduced pressure. The oil which remained was briefly subjected to slight distillation at 60°–70° C/2 mm Hg. 11 g (42.5% of theory) of O,O-diethyl-O-[1-(2-ethylmercaptoethyl)-5-chloro-1,2,4-triazol(3)yl]-thionophosphoric acid ester were obtained as a yellow oil having a refractive index $n_D^{22}$ of 1.5112.

EXAMPLE 12

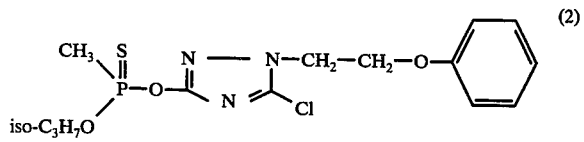

12 g (0.05 mole) of 1-(2-phenoxyethyl)-5-chloro-3-hydroxy-1,2,4-triazole were dissolved in 150 ml of absolute acetonitrile and warmed together with 8 g of potassium carbonate, to 60° C for 1 hour, while stirring. The mixture was then cooled to room temperature, 9 g of O-isopropylthionomethanephosphonic acid ester chloride were added dropwise and the whole was warmed to 60° C for 2 hours. After cooling, the reaction mixture was diluted with 500 ml of water and extracted with 200 ml of methylene chloride. The organic phase was separated off and dried over sodium sulfate. After filtering off the desiccant, the methylene chloride was stripped off under reduced pressure and the residue was briefly subjected to slight distillation at 60° C/2 mm Hg. 8 g (42.6% of theory) of O-isopropyl-O-[1-(2-phenoxyethyl)-5-chloro-1,2,4-triazol(3)yl]-thionomethanephosphonic acid ester were obtained as a yellow oil having a refractive index $n_D^{25}$ of 1.5287.

The following compounds of the formula

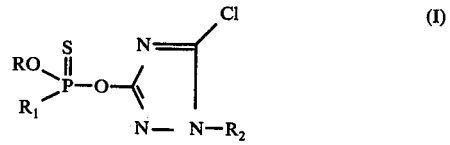

could be prepared analogously:

Table 10

| Compound No. | R | R₁ | R₂ | Yield (% of theory) | Physical data (refractive index) |
|---|---|---|---|---|---|
| 3 | C₂H₅— | C₂H₅O— | —CH(CH₃)(CO—CC₂H₅) | 79.3 | $n_D^{23}$:1.4832 |
| 4 | C₂H₅— | C₂H₅O— | —CH₂—CH₂—O—C₆H₅ | 79.0 | $n_D^{21}$:1.5325 |
| 5 | n-C₃H₇— | C₂H₅O— | —CH₂—CH₂—O—C₆H₅ | 79.1 | $n_D^{25}$:1.5279 |
| 6 | C₂H₅— | C₂H₅O— | —CH₂—CH=CH₂ | 50.5 | $n_D^{21}$:1.4962 |
| 7 | C₂H₅— | n-C₃H₇S— | —CH₂—CH₂—SC₂H₅ | 60.9 | $n_D^{25}$:1.5400 |
| 8 | iso-C₃H₇— | H₃C— | —CH₂—CH₂—SC₂H₅ | 65.4 | $n_D^{25}$:1.5269 |
| 9 | n-C₃H₇— | C₂H₅O— | —CH₂—CH₂—SC₂H₅ | 52.2 | $n_D^{25}$:1.5202 |
| 10 | C₂H₅— | iso-C₃H₇—NH— | —CH₂—CH₂—SC₂H₅ | 49.0 | $n_D^{25}$:1.5279 |
| 11 | C₂H₅— | C₂H₅O— | —CH₂—CH₂—S—C₃H₇-iso | 48.3 | $n_D^{23}$:1.5061 |
| 12 | C₂H₅— | C₂H₅— | —CH₂—CH₂—SC₃H₇-iso | 36.4 | $n_D^{25}$:1.5198 |

Table 10-continued

| Compound No. | R | $R_1$ | $R_2$ | Yield (% of theory) | Physical data (refractive index) |
|---|---|---|---|---|---|
| 13 | $C_2H_5-$ | $C_2H_5O-$ | $-CH\begin{smallmatrix}CH_3\\CH_2-CN\end{smallmatrix}$ | 42.5 | $n_D^{25}$:1.5038 |
| 14 | $C_2H_5-$ | iso-$C_3H_7$—NH— | $-CH\begin{smallmatrix}CH_3\\CH_2-CN\end{smallmatrix}$ | 41.0 | $n_D^{24}$:1.5169 |
| 15 | $C_2H_5-$ | $C_2H_5-$ | $-CH\begin{smallmatrix}CH_3\\CH_2-CN\end{smallmatrix}$ | 39.8 | $n_D^{25}$:1.5119 |
| 16 | iso-$C_3H_7-$ | $H_3C-$ | $-CH_2-CH=CH_2$ | 64.4 | $n_D^{28}$:1.5012 |
| 17 | iso-$C_3H_7-$ | $H_3C-$ | $-CH_2-CH_2-SC_3H_7$-iso | 39.9 | $n_D^{28}$:1.5246 |
| 18 | $C_2H_5-$ | iso-$C_3H_7$—NH— | $-CH_2-CH_2-SC_3H_7$-iso | 38.5 | $n_D^{26}$:1.5251 |
| 19 | $C_2H_5-$ | $C_2H_5-$ | $-CH_2-CH=CH_2$ | 67.7 | $n_D^{28}$:1.5085 |
| 20 | $C_2H_5-$ | $C_2H_5O-$ | $-CH_2-CO-OC_2H_5$ | 49.3 | $n_D^{20}$:1.4905 |
| 21 | $C_2H_5-$ | $C_2H_5O-$ | $-CH_2-CH_2-O-\bigcirc(Cl,Cl)$ | 46.9 | partially crystalline |
| 22 | iso-$C_3H_7-$ | $CH_3-$ | $-CH_2-CH_2-O-\bigcirc(Cl,Cl)$ | 62.8 | $n_D^{25}$:1.5560 |
| 23 | $C_2H_5-$ | $C_2H_5-$ | $-CH_2-CH_2-O-\bigcirc(Cl,Cl)$ | 50.2 | $n_D^{25}$:1.5611 |
| 24 | $C_2H_5-$ | $C_2H_5-$ | $-CH_2-CH_2-O-\bigcirc-Cl$ | 48.7 | $n_D^{22}$:1.5513 |
| 25 | $C_2H_5-$ | $C_2H_5O-$ | $-CH_2-CH_2-O-\bigcirc-Cl$ | 57.2 | $n_D^{22}$:1.5563 |
| 26 | iso-$C_3H_7-$ | $CH_3-$ | $-CH_2-CH_2-O-\bigcirc-Cl$ | 50.4 | $n_D^{22}$:1.5578 |
| 27 | $C_2H_5-$ | $C_2H_5O-$ | $-CH(CH_3)-CH_2-S-CH_3$ | 60.3 | $n_D^{21}$:1.5119 |
| 28 | iso-$C_3H_7-$ | $H_3C-$ | $-CH(CH_3)-CH_2-S-CH_3$ | 45.8 | $n_D^{22}$:1.5195 |

Other compounds which can be similarly prepared include:

Table 11

| Compound No. | R | $R_1$ | $R_2$ |
|---|---|---|---|
| 29 | $C_2H_5$ | $CH_3NH-$ | $-CH\begin{smallmatrix}CH_3\\CH_2-CN\end{smallmatrix}$ |
| 30 | $CH_3$ | n-$C_4H_9-O-$ | $-CH_2-O-\bigcirc(CN)$ |
| 31 | n-$C_4H_9$ | $C_2H_5-S-$ | $-CH_2-CH_2-CH_2-O-\bigcirc-S-CH_3$ |
| 32 | $C_2H_5$ | $C_4H_9$ | $-CH_2-O-\bigcirc-C_3H_7$-iso | and the like.

It will be appreciated that the instant specification and examples are set forth by way of illustration and not limitation, and that various modifications and changes may be made without departing from the spirit and scope of the present invention.

What is claimed is:

1. An O-alkyl-O-[5-chloro-1,2,4-triazol(3)yl]-thiono(thiol)phosphoric(phosphonic) acid ester or ester-amide of the formula

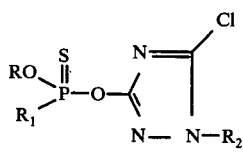

in which
R is alkyl with 1 to 6 carbon atoms,
R₁ is alkyl, alkoxy, alkylthio or monoalkylamino, each with 1 to 6 carbon atoms, and
R₂ is alkylthioalkyl with 1 to 4 carbon atoms per alkyl radical, alkenyl with 2 to 5 carbon atoms, carbalkoxyalkyl with 1 to 4 carbon atoms per alkyl radical, 1-methyl-2-cyanoethyl, or phenoxyalkyl with 1 to 4 carbon atoms in the alkyl radical and optionally substituted on the phenyl radical by at least one of halogen, cyano, or alkylthio or alkyl each with 1 to 4 carbon atoms.

2. A compound according to claim 1, in which R is alkyl with 1 to 4 carbon atoms, R₁ is alkyl, alkoxy, alkylthio or monoalkylamino each with 1 to 4 carbon atoms, and R₂ is allyl, buten-(2)-yl, buten-(3)-yl, alkylthioethyl or alkylthiopropyl with 1 to 4 carbon atoms in the alkyl radical, 1-methyl-2-cyanoethyl, carbalkoxyalkyl with 1 to 3 carbon atoms per alkyl radical, phenoxyethyl, or halophenoxyethyl.

3. The compound according to claim 1 wherein such compound is O,O-diethyl-O-[1-(1-carboethoxyethyl)-5-chloro-1,2,4-triazol(3)yl]-thionophosphoric acid ester of the formula

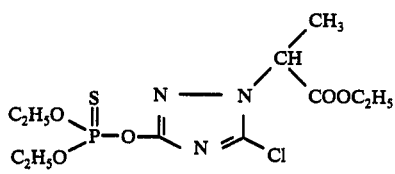

4. The compound according to claim 1 wherein such compound is, O,O-diethyl-O-[1-(2-phenoxyethyl)-5-chloro-1,2,4-triazol(3)yl]-thionophosphoric acid ester of the formula

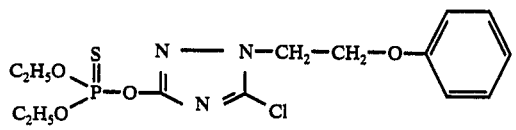

5. The compound according to claim 1 wherein such compound is O,O-diethyl-O-[1-(1-methyl-2-cyanoethyl)-5-chloro-1,2,4-triazol(3)yl]-thionophosphoric acid ester of the formula

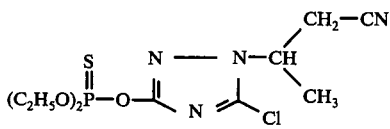

6. The compound according to claim 1 wherein such compound is O-isopropyl-O-[1-(p-chlorophenoxyethyl)-5-chloro-1,2,4-triazol(3)yl]-methanethionophosphonic acid ester of the formula

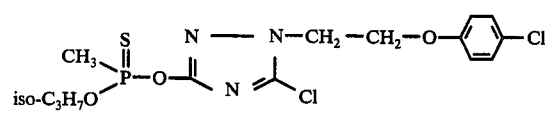

7. The compound according to claim 1 wherein such compound is O,O-di-ethyl-O-[1-methyl-2-methylmercaptoethyl]-5-chloro-1,2,4-triazol(3)yl]-thionophosphoric acid ester of the formula

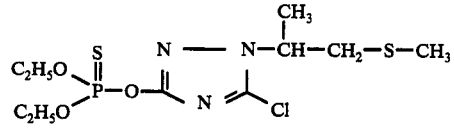

8. A nematicidal or arthropodicidal composition containing as active ingredient a nematicidally or arthropodicidally effective amount of a compound according to claim 1 in admixture with a diluent.

9. A method of combating nematodes or arthropods which comprises applying to the nematodes or arthropods, or to a habitat thereof, a nematicidally or arthropodicidally effective amount of a compound according to claim 1.

10. A method according to claim 9 in which said compound is
O,O-diethyl-O-[1-(1-carboethoxyethyl)-5-chloro-1,2,4-triazol(3)yl]-thionophosphoric acid ester,
O,O-diethyl-O-[1-(2-phenoxyethyl)-5-chloro-1,2,4-triazol(3)yl]-thionophosphoric acid ester,
O,O-diethyl-O-[1-(1-methyl-2-cyanoethyl)-5-chloro-1,2,4-triazol(3)yl]-thionophosphoric acid ester,
O-isopropyl-O-[1-(p-chlorophenoxyethyl)-5-chloro-1,2,4-triazol(3)yl]-methanethionophosphonic acid ester, or
O,O-di-ethyl-O-[1-(1-methyl-2-methylmercaptoethyl)-5-chloro-1,2,4-triazol(3)yl]-thionophophoric acid ester.

* * * * *